United States Patent [19]

Loh

[11] Patent Number: 4,554,010
[45] Date of Patent: Nov. 19, 1985

[54] 5-DEOXY-3-O-ARYLMETHYL OR SUBSTITUTED ARYLMETHYL-1,2-O-SUBSTITUTED-ALKYLIDENE-ALPHA-D-XYLOFURANOSE HERBICIDE DERIVATIVES

[75] Inventor: William Loh, Petaluma, Calif.

[73] Assignee: Chevron Research Company, San Francisco, Calif.

[21] Appl. No.: 559,126

[22] Filed: Dec. 7, 1983

[51] Int. Cl.[4] ............ A01N 43/08; C07H 17/04
[52] U.S. Cl. ............................ 71/88; 536/4.1; 536/18.1; 536/18.4
[58] Field of Search ............ 536/4.1, 18.1, 18.4; 71/88

[56] References Cited

U.S. PATENT DOCUMENTS 3,981,860 9/1976 Szhrybalo .................. 536/18.1
4,429,119 1/1984 Loh ............................ 536/4.1

Primary Examiner—Johnnie R. Brown
Assistant Examiner—Elli Peseler
Attorney, Agent, or Firm—J. A. Buchanan, Jr.; L. S. Squires

[57] ABSTRACT

5-Deoxy-3-O-arylmethyl or substituted aryl-methyl-1,2-O-substituted-alkylidene or cycloalkylidene-alpha-D-xylofuranose and 5-C-alkyl, alkylidenyl and alkenyl derivatives thereof. The compounds are useful as herbicides and plant growth regulators.

28 Claims, No Drawings

5-DEOXY-3-O-ARYLMETHYL OR SUBSTITUTED ARYLMETHYL-1,2-O-SUBSTITUTED-ALKYLIDENE-ALPHA-D-XYLOFURANOSE HERBICIDE DERIVATIVES

BACKGROUND OF THE INVENTION

This invention relates to 5-deoxy, 5-C-alkyl, 5-C-alkenyl and 5-C-alkylidene-5-deoxy-3-O-arylmethyl and substituted arylmethyl-alpha-D-xylofuranose derivatives having a substituted alkylidene or cycloalkylidene group at the 1,2-O position and to the application of such compounds as herbicides and plant growth regulators. The invention also relates to the preparation of such compounds.

The laboratory preparation of 3-O-benzyl-5-deoxy-1,2-O-isopropylidene-alpha-D-xylofuranose for the purpose of conducting academic sugar studies is referenced in Tetrahedron Letters No. 26, pp. 2447–2448 (1979). The preparation of 3-O-benzyl-5-deoxy-1,2-O-isopropylidene-5-C-propyl-alpha-D-xylofuranose as an intermediate in the multistep synthesis of the antibiotic (−)-Canadensolide is described in Tetrahedron Letters No. 35, pp. 3233–3236 (1978) and J. Chem. Soc. Jap., Chem. Ind. Chem. 1981(5), 769–775. The laboratory preparation of 3-O-benzyl-5-deoxy-5-C-methylene-1,2-O-isopropylidene-alpha-D-xylofuranose relative to certain academic studies is described in numerous publications, including Synthesis 636 (1980); Tetrahedron Letters 4841 (1979); Carbohydrate Research 48, 143 (1976) Tetrahedron Letters 2623 (1975); Helv. Chim Acta 1303 (1973); J. Chem. Soc. Perkin Trans I. 38 (1973); Carbohyd. Research 26, 230 (1973); Carbohyd. Research 22, 227 (1972); Carbohyd. Research, 215 (1970); J. Amer. Chem. Soc. 78, 2846 (1956); Carbohyd. Res. 7, 161 (1968), Methods in Carbohyd. Chem. Vol. VI 297 (1972).

The laboratory preparation of 3-O-benzyl-5-deoxy-5-C-propylidene-1,2-O-isopropylidene-alpha-D-xylofuranose is described in Tetrahedron Letters 3233 (1978) and the laboratory preparation of 3-O-benzyl-5,6-dideoxy-1,2-O-isopropylidene-5-C-methylene-alpha-D-xylo-hexofuranose is described in Helvetica Chimica Acta 58, 1501 (1975).

The laboratory preparation of 3-O-benzyl-6,7-dideoxy-1,2-O-isopropylidene-alpha-D-xylo-heptofuranos-5-ulose and/or 3-O-benzyl-6-deoxy-1,2-O-isopropylidene-alpha-D-xylo-hexofuranos-5-ulose for academic studies is described in Carbohydrate Research 31 (1973), pages 387–396; Carbohydrate Research 29 (1973), pages 11–323; Bulletin of the Chemical Society of Japan, 51 (12) (1978), pages 3595–3598; Journal of Organic Chemistry 44 (1979), pages 4294–4299; Journal of Organic Chemistry 46, (1981), pages 1296–1309; Helv. Chim. Acta 56, 1802 (1973); Carbohydrate Research 26, 441 (1973); Chem. Ber. 102, 820 (1969) and J. Org. Chem. 27, 2107 (1962).

U.S. Pat. Nos. 4,116,669, 4,146,384 and 4,330,320 and German Patent DS No. 2,860,975 disclose a broad range of tetrahydrofuran derivatives and attribute herbicidal activity to these derivatives. U.S. Pat. Nos. 3,919,252, 4,004,911 and 4,207,088 disclose dioxalane derivatives and dioxane derivatives and attribute grass herbicidal activity to these derivatives. The sodium salt of 2,3:4,6-bis-O-(1-methylethylidene)-O-(L-xylo-2-hexulofuranosonic acid) is sold as a pinching agent for azaleas and ornamentals and a growth retardant for shrubs, hedges and ground covers and is disclosed in U.S. Pat. No. 4,007,206.

The application of 5-C-alkyl-3-O-benzyl-1,2-O-isopropylidene alpha-D-xylo-pentodialdofuranose as herbicides and plant growth regulators is described by B. McCaskey in commonly assigned copending application Ser. No. 387,590 filed June 11, 1982.

In my prior copending application Ser. No. 409,236, filed Aug. 18, 1982, now U.S. Pat. No. 4,429,119, I disclosed certain 5-deoxy-3-O-arylmethyl or substituted arylmethyl-1,2-O-alkylidene-alpha-D-xylofuranose derivatives which are useful as herbicides and plant growth regulators.

SUMMARY OF THE INVENTION

The present invention provides compounds having herbicidal activity and plant growth regulating activity and provides method and compositions for preventing or retarding unwanted vegetation and for controlling the growth of vegetation. Certain of the active compounds are composed only of hydrogen, oxygen and carbon and hence are very desirable from an environmental standpoint because they decompose into innocuous carbon-oxygen moieties and water. I have further found that biological activity in tetrahydrofuranyl nucleolus compounds is very unpredictable. For example, even though the compounds and compositions of the present invention exhibit very good herbicide activity, especially grass pre-emergence herbicide activity, and plant growth regulating activity, a number of closely related analogs and even the 3-epimers of the present compounds fail to exhibit such activity. In general, the compounds of the invention exhibit superior pre-emergence grass herbicidal activity to their broadleaf and post-emergence herbicidal activity and a number of the compounds are selective pre-emergence grass herbicides with little or no broad-leaf phytotoxicity or post-emergence phytotoxicity.

In one aspect the invention provides compounds having the formula:

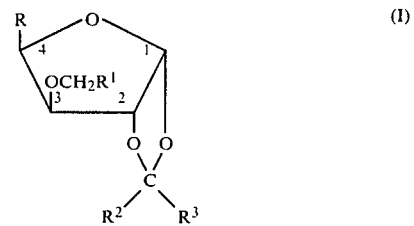

wherein R is alkyl having 1 through 4 carbon atoms or alkenyl having 2 through 4 carbon atoms;

$R^1$ is 2-trifluoromethylphenyl, aryl having 6 through 10 carbon atoms, or substituted aryl having 1 through 4 substituents independently selected from the group of lower alkyl, lower alkoxy, cyano, and halo; and one of $R^2$ or $R^3$ is lower haloalkyl having 1 through 3 halo atoms; aryl having 6 through 10 carbon atoms; substituted aryl having 1 or 2 substituents independently selected from the group of lower alkyl, lower alkoxy, halo, and trifluoromethyl; arylalkyl or substituted arylalkyl wherein the alkyl moiety has 1 or 2 carbon atoms and the aryl and substituted aryl moiety is as defined hereinabove, and the other of $R^2$ or $R^3$ is hydrogen, lower alkyl, lower haloalkyl having 1 through 3 halo atoms or aryl having 6 through 10 carbon atoms or substituted aryl having 1 or 2 substituents selected from the group of lower alkyl, halo or trifluoromethyl, arylalkyl or substituted arylalkyl wherein the alkyl moiety has 1 or 2 carbon atoms and the aryl and substituted aryl moiety is as defined hereinabove, or $R^2$ and $R^3$ together with the carbon atoms to which they are joined from a cycloalkyl group having 5 or 6 carbon atoms.

The present invention provides a herbicidal composition comprising a carrier and a herbicidally effective amount of the compound(s) of formula I.

The compounds of Formula I are (D) optically active and can comprise various isomers. Formula (I) is intended to represent the respective pure isomers as well as mixtures thereof, having the relative orientations at C-1, 2, 3 and 4 positions shown in Formula (I), and such respective isomers and mixtures are encompassed within the invention.

The present invention also provides a method for preventing or controlling the growth of unwanted vegetation, especially grasses, which comprises treating the growth medium and/or the foliage of such vegetation with a herbicidally effective amount of the compound of Formula I.

In another aspect, the present invention provides a plant growth regulating composition comprising a carrier and an effective amount of the plant growth regulating compound of the Formula I.

The present invention also provides a method for regulating plant growth which comprises treating the growth medium and/or the foliage of such vegetation with a plant growth regulating effective amount of the compound of Formula I.

The present invention also provides chemical intermediates and processes for preparing the compounds of Formula I, for example, the compounds of Formula I, wherein R is alkenyl, are useful as intermediates for the compounds of Formula I, wherein R is alkyl.

The invention will be further described hereinbelow.

FURTHER DESCRIPTION OF THE INVENTION AND THE PREFERRED EMBODIMENTS

Illustrations of typical compounds of Formula I of the present invention can be had by reference to Examples 1 and 2 set forth hereinbelow on pages 22-29. In terms of substituents the preferred compounds are those wherein R is alkyl, especially ethyl or propyl. The preferred $R^1$ substituent is aryl and monosubstituted aryl having a single substituent selected from the group lower alkyl, lower alkoxy, and halo. More preferably, $R^1$ is phenyl or 2-substituted phenyl especially phenyl, 2-methylphenyl or 2-halophenyl, especially 2-fluorophenyl and 2-chlorophenyl. Preferably, one of $R^2$ or $R^3$ is haloalkyl more preferably, fluoroalkyl, more preferably monofluoromethyl, where $R^2$ and/or $R^3$ are haloalkyl preferably the total number of halo atoms in $R^2$ plus $R^3$ is 1 through 3, more preferably 1 or 2.

The compounds of Formula I can be conveniently prepared via the following schematically represented process:

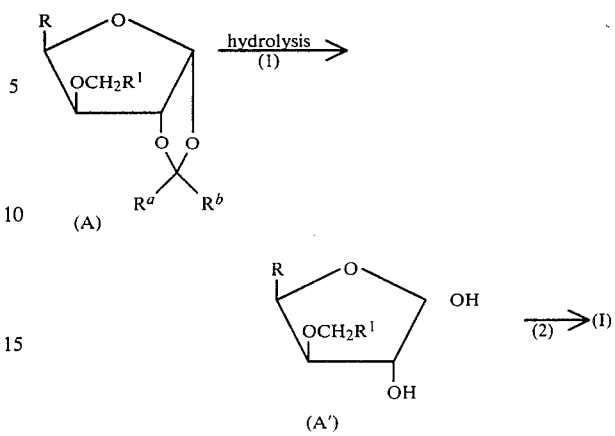

wherein $R^a$ and $R^b$ are independently hydrogen or lower alkyl or as defined for $R^2$ and $R^3$ and the wavy line indicates alpha or beta anomers at the 1-positions and anomer mixtures and R and $R^1$ are as defined hereinabove.

Generally, the starting materials of Formula A will be compounds in which $R^a$ and $R^b$ are each lower alkyl, typically methyl. However, this procedure could also be used to effect variations in the $R^1$ and/or $R^2$ groups of the compounds of the present invention.

In the first step of this process the 1,2-O-alkylidene group is cleaved. This can be effected by acid hydrolysis and typically can be effected by mild acid hydrolysis, for example, by contacting the compound with aqueous trifluoroacetic acid, preferably at room temperature (about 20°-25° C.) for about 0.5-5 hours. Conveniently, the hydrolysis can also be conducted in other aqueous acids, such as for example, aqueous acetic acid, aqueous sulfuric acid, aqueous hydrochloric acid and the like, and compatible mixtures thereof. The product A' is generally a mixture of alpha and beta anomers which, if desired, can be separated into the respective anomers, prior to conducting the second step.

The second step of this process can be effected by contacting Compound A', typically a mixture of alpha and beta anomers, with a ketone, aldehyde, ketone-acetal, or aldehyde-acetal having the desired $R^2$, $R^3$ groups, preferably in the presence of a dehydrating agent and an acid catalyst. For example, the compound of Formula I wherein one of $R^2$ or $R^3$ is methyl and the other is fluoromethyl can be prepared by using fluoroacetone.

This second step of this reaction is typically conducted at temperatures in the range of about from 25° C. to the boiling point of the ketone, aldehyde, etc. for about from 1 to 24 hours using about from 1 to 10 moles of aldehyde, ketone, aldehyde-acetal, or ketone-acetal per mole of Compound A' in the presence of a catalytic amount of acid (e.g., concentrated sulfuric acid or p-toluene-sulfonic acid) and a dehydrating agent such as, for example, anhydrous copper sulfate, or molecular sieves. This step can also be conducted in a suitable inert organic solvent, such as, for example, toluene, benzene, and xylene. This can also be conveniently conducted in situ with the first step after evaporation of aqueous acids.

The compounds of Formula A can be prepared via the process schematically represented by the following overall reaction equation:

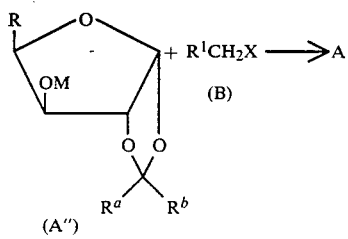

(B)

(A'')

wherein R, $R^1$, $R^a$ and $R^b$ are as defined hereinabove, X is chloro, bromo or iodo, and M is an alkali metal cation preferably sodium.

This process can be effected by contacting compound A'' with compound B, having the appropriate $R^1$ group, preferably in an inert organic solvent (e.g., tetrahydrofuran) and in the presence of an appropriate catalyst. This process is typically conducted at temperatures in the range of about from 0° to 140° C., preferably about from 25° to 75° C., for about from 1 to 48 hours, preferably about from 3 to 12 hours. Typically about from 1.0 to 1.25 moles, and preferably about from 1.0 to 1.1 moles of (B) are used per mole of compound A''.

Suitable inert organic solvents which can be used include, for example, tetrahydrofuran, ethyl ether, xylene, toluene, dimethylsulfoxide, dimethylformamide, and the like and compatible mixtures thereof. Suitable catalysts which can be used include, for example, tetrabutylammonium iodide, tetrabutylammonium bromide, benzyltriethylammonium chloride, and tricaprylylmethylammonium chloride, and the like. Typically a catalyst to reactant (A'') ratio of about from 0.01 to 0.1 mole of catalyst per mole of A'' is used. Generally, best results are obtained using tetrahydrofuran as the solvent, tetrabutylammonium iodide as the catalyst and conducting the reaction at about from 25° to 65° C. for about from 3 to 12 hours. Compound A can be separated from the reaction product mixture via any suitable procedure; for example, chromatographically. For example, the separation of the compound of Formula A, wherein R is methyl, $R^1$ is phenyl and $R^a$ and $R^b$ are each methyl, is described in Tetrahedron Letters No. 26, pp. 2447–2448 (1979).

This process could also be applied to prepare the compounds of Formula I wherein one of $R^2$ or $R^3$ is hydrogen, however, because of interfering reactions such compounds are best prepared from the corresponding compounds of Formula A', as described hereinabove.

Compound A'' can be conveniently prepared by reacting the corresponding 3-position hydroxy compound (i.e., M is hydrogen) with an alkali metal base such as sodium hydride, potassium hydride, sodium hydroxide; potassium hydroxide and the like. Typically, this reaction is conducted at about from 0° to 140° C. preferably about from 0° to 65° C., for about from 0.5 to 12 hours, preferably 0.5 to 1 hour, using about from 1.0 to 1.1 moles of alkali metal base per mole of the hydroxy analog of compound A''. Conveniently, the same inert organic solvents as described above are also used thus facilitating *in situ* preparation of compound A as described above. The appropriate 3-hydroxy analogs wherein R is alkyl having 2 through 4 carbon atoms can be prepared via the following schematically represented process:

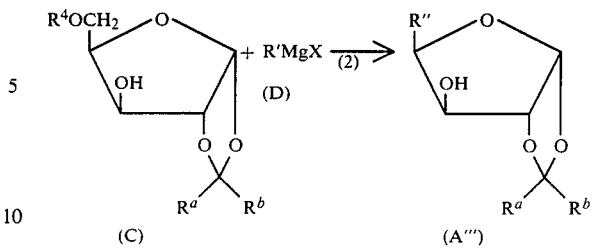

(C)   (A''')

wherein R' is alkyl having 1 through 3 carbon atoms; R'' is alkyl having 2 through 4 carbon atoms; $R^4O$ is an easily replaced group; X is chloro, bromo, or iodo and $R^a$ and $R^b$ are as defined hereinabove.

The first step of this process can be effected by contacting compound (C) with a Grignard reagent (D) having the appropriate R' group, preferably in an inert organic solvent (e.g., ethyl ether) and in the presence of a suitable catalyst. This step is typically conducted at temperatures in the range of about from −78° to 65° C. preferably about from 25° to 65° C. for about from 1 to 24 hours. Conveniently the reaction is conducted using about from 2 to 20 preferably about from 5 to 8 moles of compound D per mole of compound C.

Suitable inert organic solvents which can be used include, for example, ethyl ether and tetrahydrofuran and the like and compatible mixtures thereof. Suitable catalysts which can be used include, for example, dilithium tetrachlorocuprate ($Li_2CuCl_4$); ferric chloride, and the like and compatible mixtures thereof. Typically, a catalyst ratio of about from 0.001 to 0.01 mole of catalyst is used per mole of compound C.

As indicated above $R^4O$ is a group which is easily replaced by the R' moiety of the Grignard reagent. $R^4$ can, for example, be the group having the formula $$-\overset{\overset{O}{\|}}{\underset{\underset{O}{\|}}{S}}R^5$$

wherein $R^5$ is phenyl, 4-methylphenyl, lower alkyl.

Very good results are typically obtained when $R^4$ is tosyl or mesyl. The compounds of Formula C are generally known compounds and can be prepared by known procedures or by obvious modifications thereof. For example, the compounds of Formula C wherein $R^4$ is tosyl or hydrogen and $R^2$ and $R^3$ are each methyl are described in Methods in Carbohydrate Chem. Vol. II 249 (1963). Analogs having diffezent $R^4$ leaving groups can be obtained by reacting the 5-position hydroxy compound with a halide derivative of the leaving group. The 1,2-O-isopropylidene substituent in the starting material can be prepared by reacting the corresponding known 1,2,3,5-tetrahydroxy analog with dimethyl ketone to yield the corresponding 1,2:3,5-di-O-isopropylidene analog, see J. Amer. Chem. Soc. 77, 5900 (1955). The 3,5-O-alkylidene group can be selectively cleaved without cleaving the 1,2-O-alkylideoe group by mild acid hydrolysis, see also J. Amer. Chem. Soc., 77, 5900 (1955). 1,2-O-Isopropylidene-alpha-D-xylofuranose is also available commercially. Variation in the $R^2$ and $R^3$ substituents can be obtained by replacing dimethyl ketone with the appropriate ketone or aldehyde ketone-acetal or aldehyde-acetal, for example, diethyl ketone, acetaldehyde, formaldehyde, propionaldehyde diethyl acetal, acetone dimethyl acetal, acetaldehyde diethyl acetal, methyl ethyl ketone, etc.

The compounds of Formula A''' wherein R'' is methyl can be obtained by the process schematically represented by the following overall reaction sequence:

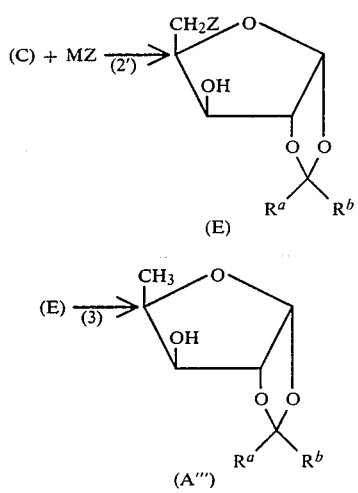

wherein M, $R^a$ and $R^b$ are as defined hereinabove, and Z is iodo or bromo.

Step 2' can be effected by contacting compound C with an alkali metal bromide or iodide (for example, sodium iodide) preferably a suitable inert organic solvent. This process is typically conducted at temperatures in the range of about from 50° to 100° C., preferably about from 80° to 90° C. for about from 5 to 48 hours. Typically about from 1.0 to 5.0, preferably about from 1.5 to 2.0 moles of alkali halide are used per mole of compound (C). Suitable inert organic solvents which can be used include for example 2-butanone, 2-pentanone, 3-pentanone, and the like. Conveniently, the reaction is conducted at the reflux temperature of the solvent. The synthesis of 5-deoxy-5-iodo-1,2-O-isopropylidene-alpha-D-xylofuranose where Z is iodo and $R^a$ and $R^b$ are each methyl is also described in J. Med. Chem. 22, 28 (1979).

Step 3 is conducted by contacting compound E with hydrogen in the presence of a suitable hydrogenation catalyst preferably in an inert organic solvent and preferably in the presence of a suitable scavenger base. This reaction is typically conducted at temperatures in the range of about from 0° to 50° C., conveniently 15° to 30° C., for about from 1 to 5 hours at 10–20 psi of hydrogen pressure. Suitable inert organic solvents which can be used include, for example, lower alkanols (e.g. methanol), and ethanol, ethyl acetate, and the like and compatible mixtures thereof.

Since this process yields hydrogen iodide or hydrogen bromide as a byproduct, it is preferred to conduct the reaction in the presence of a scavenger base to react with the hydrogen halide byproduct. Suitable scavenger bases which can be used include, for example, triethylamine, pyridine, and the like and compatible mixtures thereof.

Step 3 can also be conducted by employing LiAlH$_4$ as the reducing agent. The synthesis of 5-deoxy-1,2-O-isopropylidene-alpha-D-xylofuranose is also described in J. Chem. Soc. 2140 (1953).

Variation in the 1,2-O-alkylidene ether group can be effected as already described hereinabove.

The compounds of Formula I wherein R is isopropyl can be prepared by the following schematically represented process:

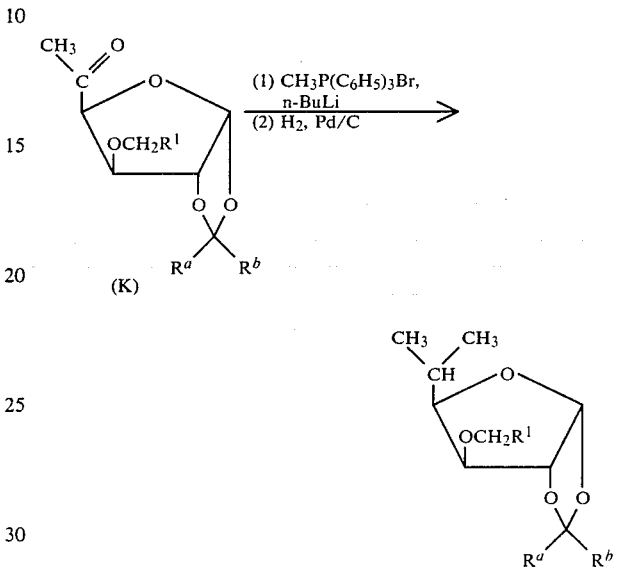

The first step of this process can be effected by contacting the compound of Formula K with triphenylmethyl phosphonium bromide and n-butyllithium preferably in an inert organic solvent. Typically, this step is conducted at temperatures in the range of about from 0° to 70° C., preferably about from 20° to 30° C., using about from 0.8 to 3 moles of triphenylmethyl phosphonium bromide and about from 0.5 to 3 moles of butyllithium per mole of compound K. Suitable solvents which can be used, include for example, tetrahydrofuran, benzene, hexane, dimethylsulfoxide, dimethoxyethane and the like. The alkene product of this reaction can be separated or desired as the product or hydrogenated to the alkyl. The second step is thus conducted by contacting the alkene reaction product with hydrogen in the presence of a suitable hydrogenation catalyst (for example palladium on carbon) in an inert organic solvent. Typically, the hydrogenation is conducted at temperatures in the range of about from 15° to 50° C. at 10–20 psi of hydrogen pressure. Typically, the reaction is conducted by simply contacting the alkene product with hydrogen until no further hydrogen is taken up. The same inert organic solvents as used for the first step can also be used for the hydrogenation and the hydrogenation can be conveniently conducted in situ.

Variation in the 1,2-O-alkylidene group can be effected as described hereinabove.

The compounds of Formula I wherein R is vinyl can be prepared by the process schematically represented by the following overall reaction equation sequence:

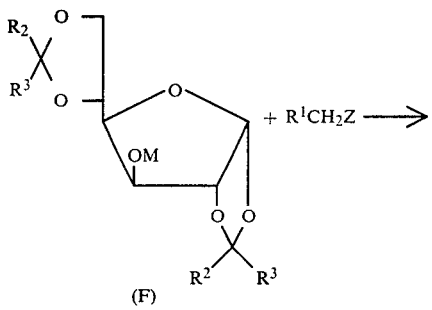

(F)

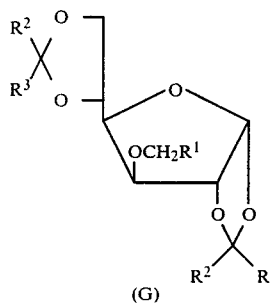

(G)

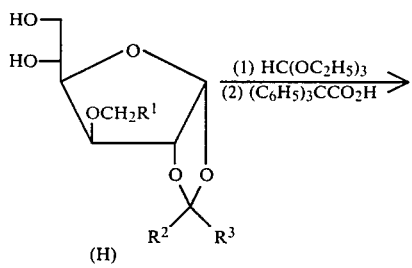

(H)

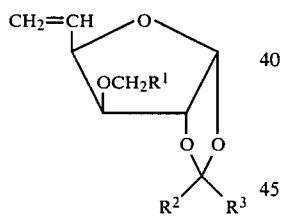

wherein $R^1$, $R^2$, $R^3$, M, and Z are as defined hereinabove.

The first step of this process can be effected in the same manner as described hereinabove, with respect to the reaction of compound A''' to compound A.

The starting material of Formula F can be prepared from the known 1,2,3,5,6,-pentahydroxy substrate by reaction with the appropriate ketone as already described above.

In the next step the 5,6-O-alkylidenyl group is selectively cleaved without cleaving the 1,2-O-alkylidenyl group. This can be conveniently effected by mild acid hydrolysis, for example, by contacting compound G with aqueous acetic acid at temperatures in the range of about from 25° to 100° C.; preferably about from 40° to 60° C. for about from 1 to 48 hours. The hydrolysis can also be conducted, for example, in aqueous trifluoroacetic acid, aqueous hydrochloric acid, and the like, and compatible mixtures thereof. The preparation of the compounds of Formulas F, G, and H, wherein $R^1$ is phenyl and $R^2$ and $R^3$ are each methyl, is also described in Methods in Carbohydrate Chem. Vol. VI 286 and 297 (1972).

The last step, conversion of the 5,6-dihydroxy group to the olefin, is conveniently conducted in two phases. The first phase can be conducted by contacting compound H with a trialkylorthoformate (e.g. triethylorthoformate) under protic conditions to yield the corresponding 5,6-O-alkoxyalkylidene derivative of compound H.

This phase is conveniently conducted at temperatures in the range of about from 100° C. to the boiling point of the trialkylorthoformate, preferably 120° to 146° C. for about from 3 to 12 hours. Preferably, small amount of a weak acid (e.g. acetic acid) is added to the reaction mixture to ensure protic conditions.

The next phase of this step can be effected by heating the product of the first phase in the presence of an acid. This phase is typically conducted at temperatures in the range of about from 160° to 180° C. for about from 3 to 6 hours. Suitable acids which can be used include, for example, triphenylacetic acid, benzoic acid, p-chlorobenzoic acid, and the like. The example wherein $R^1$ is phenyl, and $R^2$ and $R^3$ are each methyl, is described in Methods in Carbohydrate Chem. Vol. VI 297 (1972).

The compounds of Formula I wherein R is alkenyl having 3 or 4 carbon atoms having its double bond at the 1' position can be made by the following procedure:

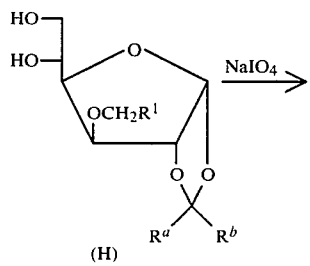

(H)

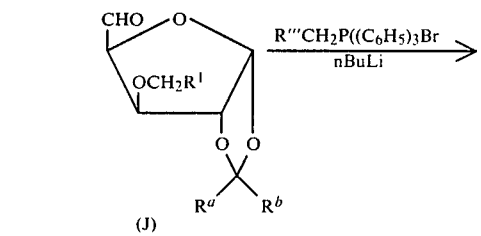

(J)

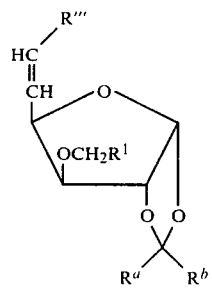

wherein R''' is alkyl having 1 to 2 carbon atoms; and $R^1$, $R^a$, and $R^b$ are as defined hereinabove.

This first step of this process can be effected by contacting compound (H) with an alkali metal metaperiodate (e.g. sodium metaperiodate) or lead tetraacetate preferably in an inert organic solvent. Typically, this process is conducted at temperatures in the range of about from 0° to 70° C., preferably 0° to 30° C. using about from 1.0 to 1.25 moles of alkali metal metaperiodate per mole of compound (H). Suitable solvents which can be used include, for example, tetrahydrofuran, methanol, ethanol, benzene, toluene, water, and the like.

The second step can be effected by contacting compound J with triphenylethyl or triphenylpropyl phosphonium bromide and n-butyllithium, preferably in an inert organic solvent. Typically, this process is conducted at temperatures in the range of about from 0° to 70° C., preferably 20° to 30° C., using about from 0.8 to 3 moles of the bromide and about from 0.5 to 3 moles of butyllithium per mole of compound (J). Suitable inert organic solvents which can be used include, for example, tetrahydrofuran, benzene, hexane, dimethylsulfoxide, dimethoxyethane, and the like.

The preparation of the compound wherein R''' is ethyl, $R^1$ is phenyl and $R^a$ and $R^b$ are each methyl, is also described in Tetrahedron Letters No. 35, pp. 3233–3236 (1978).

The compounds of Formula (I) wherein R is alkenyl having its unsaturation at the 2' position can be prepared by contacting the corresponding compound of Formula I but wherein R is formylmethyl [Helv. Chim. Acta 63, 1644 (1980)] with triphenylmethyl or triphenylethyl, phosphonium bromide and butyllithium in an inert organic solvent (e.g. tetrahydrofuran). This reaction can be conducted in the same manner as described for the second step hereinabove.

The compounds of Formula (I) wherein R is alkenyl having its unsaturation at the 3' position can be prepared by contacting the corresponding compound of Formula I but wherein R is p-toluenesulfonyloxymethyl with the Grignard reagent of allyl bromide or chloride preferably in an inert organic solvent (e.g., ethyl ether or tetrahydrofuran) and in the presence of a suitable catalyst in the same manner as the Grignard reaction as previously described above.

The compounds of Formula I wherein R is alkyl having 2 to 4 carbon atoms can also be made by hydrogenation of the corresponding R is alkenyl compound, for example, via hydrogenation in the presence of a suitable hydrogenation catalyst such as, for example, palladium on carbon.

GENERAL PROCESS APPLICATIONS

In the above-described processes, it is generally preferable to separate the respective products before proceeding with the next step in the reaction sequence unless expressly stated otherwise. These products can be recovered from their respective reaction product mixtures by any suitable separation and purification procedure, such as, for example, recrystallization and chromatography. Suitable separation and purification procedures are, for example, illustrated in the Examples set forth hereinbelow. Also generally it is preferred to use the appropriate isomer starting material having the same orientation as Compound I. However, isomer mixtures of starting materials can also be used. In this case the product will be a mixture of Compound I and its isomers. Compound I can then be separated from the isomer mixture or applied as a mixture. Also, it is generally peferable to effect the desired 1,2-O-substitution as the last step in preparation of Compound I.

Generally, the reactions described above are conducted as liquid phase reaction and hence pressure is generally not significant except as it affects temperature (boiling point) where reactions are conducted at reflux. Therefore, these reactions are generally conducted pressures of from 300 to 3000 mm of mercury and conveniently are conducted at about atmospheric or ambient pressure. In the case of the hydrogenation described above, the hydrogenation is typically conducted by bubbling hydrogen through the substrate, dissolved in a solvent, or placing the substrate solution under hydrogen. Thus, the hydrogenation is typically conducted under a modest pressure, typically about from 800 to 3000 mm Hg.

It should also be appreciated that where typical or preferred process conditions (e.g., reaction temperatures, times, mol ratios of reactants, solvents, etc.) have been given, that other process conditions could also be used, although typically with poor yields or economies. Optimum reaction conditions (e.g., temperature, reaction time, mol ratios, solvents, etc.) may vary with the particular reagents or organic solvents used but can be determined by routine optimization procedures.

Where optical isomer mixtures are obtained, the respective optical isomers can be obtained by conventional resolution procedures, for example, by converting the isomer mixture to an acid derivative and reacting with an optically active base which will yield a mixture of optical salts, of the desired compound, which can be resolved by conventional procedures (e.g., crystallization) into the respective plus and minus optical salts.

DEFINITIONS

As used herein the following terms have the following meanings unless expressly stated to the contrary:

The term "lower alkyl" refers to both straight- and branched-chain alkyl groups having a total of from 1 through 4 carbon atoms and includes primary, secondary and tertiary alkyl groups. Typical lower alkyls include, for example, methyl, ethyl, n-propyl, isopropyl, n-butyl, t-butyl.

The term "lower alkenyl" refers to alkenyl groups having 2 through 4 carbon atoms and includes for example vinyl; 1-propenyl, 2-propenyl, 1-butenyl, 2-methylprop-1-enyl and the like.

The term "halo" refers to the group of fluoro, chloro, bromo and iodo.

The term "aryl" refers to aryl groups having 6 through 10 carbon atoms and includes, for example, phenyl, naphthyl, indenyl, and the like.

The term "substituted aryl" refers to aryl groups having 1 or 2 substituents independently selected from the group of lower alkyl, lower alkoxy and halo. Typical substituted aryl includes, for example, 2-fluorophenyl, 2-chlorophenyl, 2,6-dimethylphenyl, 2-methylphenyl, 2,4-dimethylphenyl, 2,5-dimethylphenyl, 2,4-dichlorophenyl, 2-methoxyphenyl and the like.

The term "arylalkyl" refers to the groups —CH$_2$Ar; —CH$_2$CH$_2$Ar and —CH(CH$_3$)Ar wherein Ar is aryl.

The term "substituted arylalkyl" or "ring substituted arylalkyl" refers to the groups —CH$_2$Ar'; —CH$_2$CH$_2$Ar' and —CH(CH$_3$)Ar' wherein Ar' is substituted aryl.

As exemplary of the sugar nomenclature used herein the term "3-O-benzyl-1,2-O-[1-(fluoromethyl)ethylidene]-5-deoxy-5-C-methyl-alpha-D-xylofuranose" refers to the compound having the following structural formula:

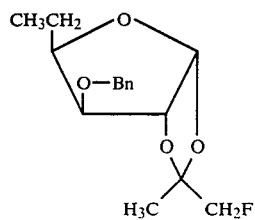

wherein Bn is benzyl.

UTILITY

The compounds of Formula I exhibit very good pre-emergence against grasses and also in some cases exhibit modest pre-emergence activity against broad-leaf plants and post-emergence herbicidal activity. Further, by proper reduction of the dosage, the compounds can be safely applied as selective pre-emergence grass herbicides to prevent or reduce the growth of grasses amongst broad leaf crops such as soybean. The preferred herbicidal compounds of Formula I are those wherein R is ethyl or propyl and especially the compound wherein R is ethyl.

Generally, for post-emergent applications, the herbicidal compounds are applied directly to the foliage or other plant parts. For pre-emergence applications, the herbicidal compounds are applied to the growing medium, or prospective growing medium, of the plant. The optimum amount of the herbicidal compound or composition will vary with the particular plant species, and the extent of part plant growth and the particular part of the plant which is contacted. The optimum dosage will also vary with the general location, or environment, of application (e.g., sheltered areas such as greenhouses compared to exposed areas such as fields), and type and degree of control desired. Generally, for both pre- and post-emergent control, the present compounds are applied at rates of about from 0.2 to 60 kg/ha, preferably about from 0.5 to 10 kg/ha.

Also, although in theory the compounds can be applied undiluted, in actual practice they are generally applied as a composition or formulation comprising an effective amount of the compound(s) and an acceptable carrier. An acceptable carrier (algriculturally acceptable carrier) is one which does not significantly adversely affect the desired biological effect achieved by the active compounds, save to dilute it. Typically, the composition contains about from 0.05 to 95% by weight of the compound of Formula (I) or mixtures thereof. Concentrates can also be made having higher concentrations designed for dilution prior to application. The carrier can be a solid, liquid, or aerosol. The actual compositions can take the form of granules, powders, dusts, solutions, emulsions, slurries, aerosols, and the like.

Suitable solid carriers which can be used include, for example, natural clays (such as kaolin, attapulgite, montmorillonite, etc.), talcs, pyrophyllite, diatomaceous silica, synthetic fine silica, calcium aluminosilicate, tricalcium phosphate, and the like. Also, organic materials, such as, for example, walnut shell flour, cotton-seed hulls, wheat flour, wood flour, wood bark flour, and the like can also be used as carriers. Suitable liquid diluents which can be used include, for example, water, organic solvents (e.g., hydrocarbons such as benzene, toluene, dimethylsulfoxide, kerosene, diesel fuel, fuel oil, petroleum naphtha, etc.), and the like.

Suitable aerosol carriers which can be used include conventional aerosol carriers such as halogenated alkanes, etc.

The composition can also contain various promoters and surface-active agents which enhance the rate of transport of the active compound into the plant tissue such as, for example, organic solvents, wetting agents and oils, and in the case of compositions designed for pre-emergence application agents which reduce the leachability of the compound.

The composition can also contain various compatible adjuvants, stabilizers, conditioners, insecticides, fungicides, and if desired, other herbicidally active compounds.

The compounds of the present invention also exhibit plant growth regulating activity and especially root growth inhibition; foliage regrowth inhibition and crop enhancement. The former activity is useful where top growth is desirable. Foliage regrowth inhibition is desirable in cases such as the harvesting of cotton. In harvesting cotton, defoliants and desiccants are frequently used to remove the leaves of the cotton plant thus making the cotton more accessible. In such cases regrowth inhibitors are useful to inhibit the regrowth of leaves, before harvesting is completed. Crop enhancement is produced by pinching and increasing crop bearing branching in crops such as soy bean.

The present compounds of Formula I can be applied in pure form, but more pregmatically, as in the case of herbicide application, are applied in combination with a carrier. The same types of carriers as set forth hereinabove with respect to the herbicide compositions can also be used. Depending on the desired application, the plant growth regulating composition can also contain, or be applied in combination with other compatible ingredients such as desiccants, defoliants, surface-active agents, adjuvants, fungicides, insecticides and selective herbicides. Typically, the plant growth regulating composition will contain a total of about from 0.005 to 90 wt. %, of the compound(s) of Formula (Ia) depending on whether the composition is intended to be applied directly or diluted first.

A further understanding of the invention can be had in the following non-limiting Preparation and Examples. Wherein, unless expressly stated to the contrary, all temperatures and temperature ranges refer to the Centigrade system and the term "ambient" or "room temperature" refers to about 20°-25° C. The term "percent" or "%" refers to weight percent and the term "mole" or "moles" refers to gram moles. The term "equivalent" refers to a quantity of reagent equal in moles, to the moles of the preceding or succeeding reactant recited in that example in terms of finite moles or finite weight or volume. Also where necessary examples are repeated to provide additional starting material for subsequent examples.

EXAMPLE 1

3-O-Benzyl-1,2-O-[1-(fluoromethyl)ethylidene]-5-deoxy-5-C-methyl-alpha-D-xylofuranose In this example, 40 ml of 9:1 parts by volume mixture of trifluoroacetic acid and water was added to 5.6 g (0.02 mol) of 3-O-benzyl-1,2-O-isopropylidene-5-deoxy-5-C-methyl-alpha-D-xylofuranose. The resulting mixture was stirred for three hours at room temperature and then evaporated at 50°-55° C. affording 3-O-benzyl-5-deoxy-5-C-methyl-alpha-and beta-D-xylofuranose as a yellow liquid.

A mixture containing 0.02 mol of 3-O-benzyl-5-deoxy-5-C-methyl-alpha-and beta-D-xylofuranose, 2.3 g (0.03 mol) of fluoroacetone, 3 g of anhydrous copper sulfate and about 0.2 to 0.3 ml of concentrated sulfuric acid was stirred at room temperature for about 16–18 hours. Two hundred (200) ml of ethyl ether was then added followed by the addition of saturated aqueous sodium bicarbonate solution. The ethyl ether layer was separated from the water layer, washed with aqueous sodium bisulfite solution and then washed three times with water. The ethyl ether layer was then dried over magnesium sulfate and concentrated by evaporation affording the title compound as a partially crystallized product.

Similarly, the compounds listed below can be prepared by following the same procedure using as starting materials the corresponding substituted alpha-X-xylofuranose derivatives. (Such derivatives can, for example, be prepared via the procedures described in Applicant's copending application Serial No. 409,236, filed August 18, 1982, which procedures are hereby incorporated by reference):

3-O-benzyl-1,2-O-[1-(fluoromethyl)ethylidene]-5-deoxy-alpha-D-xylofuranose;

3-O-benzyl-1,2-O-[1-(fluoromethyl)ethylidene]-5-deoxy-5-C-ethyl-alpha-D-xylofuranose;

3-O-benzyl-1,2-O-[1-(fluoromethyl)ethylidene]-5-deoxy-5,5-C-dimethyl-alpha-D-xylofuranose;

3-O-benzyl-1,2-O-[1-(fluoromethyl)ethylidene]-5-deoxy-5-C-propyl-alpha-D-xylofuranose;

3-O-benzyl-1,2-O-[1-(fluoromethyl)ethylidene]-5-deoxy-5-C-methylene-alpha-D-xylofuranose (i.e., R=vinyl);

3-O-benzyl-1,2-O-[1-(fluoromethyl)ethylidene]-5-deoxy-5-C-vinyl-alpha-D-xylofuranose (i.e., R=allyl);

3-O-(2-fluorobenzyl)-1,2-O-[1-(fluoromethyl)ethylidene]-5-deoxy-5-C-methyl-alpha-D-xylofuranose;

3-O-(2-fluorobenzyl)-1,2-O-[1-(fluoromethyl)ethylidene]-5-deoxy-alpha-D-xylofuranose;

3-O-(2-fluorobenzyl)-1,2-O-[1-(fluoromethyl)ethylidene]-5-deoxy-5-C-ethyl-alpha-D-xylofuranose;

3-O-(2-fluorobenzyl)-1,2-O-[1-(fluoromethyl)ethylidene]-5-deoxy-5,5-C-dimethyl-alpha-D-xylofuranose;

3-O-(2-fluorobenzyl)-1,2-O-[1-(fluoromethyl)ethylidene]-5-deoxy-5-C-propyl-alpha-D-xylofuranose;

3-O-(2-fluorobenzyl)-1,2-O-[1-(fluoromethyl)ethylidene]-5-deoxy-5-C-methylene-alpha-D-xylofuranose (i.e., R=vinyl);

3-O-(2-fluorobenzyl)-1,2-O-[1-(fluoromethyl)ethylidene]-5-deoxy-5-C-vinyl-alpha-D-xylofuranose (i.e., R=allyl);

3-O-(2-chlorobenzyl)-1,2-O-[1-(fluoromethyl)ethylidene]-5-deoxy-5-C-methyl-alpha-D-xylofuranose;

3-O-(2-chlorobenzyl)-1,2-O-[1-(fluoromethyl)ethylidene]-5-deoxy-alpha-D-xylofuranose;

3-O-(2-chlorobenzyl)-1,2-O-[1-(fluoromethyl)ethylidene]-5-deoxy-5-C-ethyl-alpha-D-xylofuranose;

3-O-(2-chlorobenzyl)-1,2-O-[1-(fluoromethyl)ethylidene]-5-deoxy-5,5-C-dimethyl-alpha-D-xylofuranose;

3-O-(2-chlorobenzyl)-1,2-O-[1-(fluoromethyl)ethylidene]-5-deoxy-5-C-propyl-alpha-D-xylofuranose;

3-O-(2-chlorobenzyl)-1,2-O-[1-(fluoromethyl)ethylidene]-5-deoxy-5-C-methylene-alpha-D-xylofuranose (i.e., R=vinyl);

3-O-(2-chlorobenzyl)-1,2-O-[1-(fluoromethyl)ethylidene]-5-deoxy-5-C-vinyl-alpha-D-xylofuranose (i.e., R=allyl);

3-O-(3-methoxybenzyl)-1,2-O-[1-(fluoromethyl)ethylidene]-5-deoxy-5-C-methyl-alpha-D-xylofuranose;

3-O-(3-methoxybenzyl)-1,2-O-[1-(fluoromethyl)ethylidene]-5-deoxy-alpha-D-xylofuranose;

3-O-(3-methoxybenzyl)-1,2-O-[1-(fluoromethyl)ethylidene]-5-deoxy-5-C-ethyl-alpha-D-xylofuranose;

3-O-(3-methoxybenzyl)-1,2-O-[1-(fluoromethyl)ethylidene]-5-deoxy-5,5-C-dimethyl-alpha-D-xylofuranose;

3-O-(3-methoxybenzyl)-1,2-O-[1-(fluoromethyl)ethylidene]-5-deoxy-5-C-propyl-alpha-D-xylofuranose;

3-O-(3-methoxybenzyl)-1,2-O-[1-(fluoromethyl)ethylidene]-5-deoxy-5-C-methylene-alpha-D-xylofuranose (i.e., R=vinyl);

3-O-(3-methoxybenzyl)-1,2-O-[1-(fluoromethyl)ethylidene]-5-deoxy-5-C-vinyl-alpha-D-xylofuranose (i.e., R=allyl);

3-O-(2,6-dimethylbenzyl)-1,2-O-[1-(fluoromethyl)ethylidene]-5-deoxy-5-C-methyl-alpha-D-xylofuranose;

3-O-(2,6-dimethylbenzyl)-1,2-O-[1-(fluoromethyl)ethylidene]-5-deoxy-alpha-D-xylofuranose;

3-O-(2,6-dimethylbenzyl)-1,2-O-[1-(fluoromethyl)ethylidene]-5-deoxy-5-C-ethyl-alpha-D-xylofuranose;

3-O-(2,6-dimethylbenzyl)-1,2-O-[1-(fluoromethyl)ethylidene]-5-deoxy-5,5-C-dimethyl-alpha-D-xylofuranose;

3-O-(2,6-dimethylbenzyl)-1,2-O-[1-(fluoromethyl)ethylidene]-5-deoxy-5-C-propyl-alpha-D-xylofuranose;

3-O-(2,6-dimethylbenzyl)-1,2-O-[1-(fluoromethyl)ethylidene]-5-deoxy-5-C-methylene-alpha-D-xylofuranose (i.e., R=vinyl);

3-O-(2,6-dimethylbenzyl)-1,2-O-[1-(fluoromethyl)ethylidene]-5-deoxy-5-C-vinyl-alpha-D-xylofuranose (i.e., R=allyl);

3-O-(2-naphthamethylbenzyl)-1,2-O-[1-(fluoromethyl)ethylidene]-5-deoxy-5-C-methyl-alpha-D-xylofuranose;

3-O-(2-naphthamethyl)-1,2-O-[1-(fluoromethyl)ethylidene]-5-deoxy-alpha-D-xylofuranose;

3-O-(2-naphthamethyl)-1,2-O-[1-(fluoromethyl)ethylidene]-5-deoxy-5-C-ethyl-alpha-D-xylofuranose;

3-O-(2-naphthamethyl)-1,2-O-[1-(fluoromethyl)ethylidene]-5-deoxy-5,5-C-dimethyl-alpha-D-xylofuranose;

3-O-(2-naphthamethyl)-1,2-O-[1-(fluoromethyl)ethylidene]-5-deoxy-5-C-propyl-alpha-D-xylofuranose;

3-O-(2-naphthamethyl)-1,2-O-[1-(fluoromethyl)ethylidene]-5-deoxy-5-C-methylene-alpha-D-xylofuranose (i.e., R=vinyl);

3-O-(2-naphthamethyl)-1,2-O-[1-(fluoromethyl)ethylidene]-5-deoxy-5-C-vinyl-alpha-D-xylofuranose (i.e., R=allyl).

Similarly, by following the same procedure but respectively using fluoroacetaldehyde; 1,6-dibromohexan-3-one; 2'-chlorophenylacetone; benzaldehyde; 1,6-diphenylpentan-3-one cyclopentanone and cyclohexanone, the corresponding 1,2-O-(2-fluoroethylidene); 1,2-O-{[1-(2-bromoethyl)-4-bromo]butylidene}; 1,2-O-[1-(2-chlorobenzyl)ethylidene]; 1,2-O-benzylidene; 1,2-O-{[3-phenyl-1-(2-phenethyl)]propylidene}; cyclopentylidene and cyclohexylidene analogs of the above compounds can also be made, for example:

3-O-benzyl-1,2-O-(2-fluoroethylidene)-5-deoxy-5-C-methyl-alpha-D-xylofuranose;

3-O-benzyl-1,2-O-{[1-(2-bromoethyl)-4-bromo]butylidene}-5-deoxy-alpha-D-xylofuranose;

3-O-benzyl-1,2-O-[1-(2-chlorobenzyl)ethylidene]-5-deoxy-5-C-ethyl-alpha-D-xylofuranose;

3-O-benzyl-1,2-O-benzylidene-5-deoxy-5,5-C-dimethylalpha-D-xylofuranose;

3-O-benzyl-1,2-O-{[3-phenyl-1-(2-phenethyl)]propylidene}-5-deoxy-5-C-propyl-alpha-D-xylofuranose;

3-O-benzyl-1,2-O-cyclopentylidene-5-deoxy-5-C-methylene-alpha-D-xylofuranose (i.e., R=vinyl);

3-O-benzyl-1,2-O-cyclohexylidene-5-deoxy-5-C-vinylalpha-D-xylofuranose (i.e., R=allyl);

3-O-(2-fluorobenzyl)-1,2-O-(2-fluoroethylidene)-5-deoxy-5-C-methyl-alpha-D-xylofuranose;

3-O-(2-fluorobenzyl)-1,2-O-[1-(2-bromoethyl)-4-bromo]butylidene-5-deoxy-alpha-D-xylofuranose;

3-O-(2-fluorobenzyl)-1,2-O-[1-(2-chlorobenzyl)ethylidene]-5-deoxy-5-C-ethyl-alpha-D-xylofuranose;

3-O-(2-fluorobenzyl)-1,2-O-benzylidene-5-deoxy-5,5-C-dimethyl-alpha-D-xylofuranose;

3-O-(2-fluorobenzyl)-1,2-O-{[(3-phenyl-1-(2-phenethyl))propylidene}-5-deoxy-5-C-propyl-alpha-D-xylofuranose;

3-O-(2-fluorobenzyl)-1,2-O-cyclopentylidene-5-deoxy-5-C-methylene-alpha-D-xylofuranose (i.e., R=vinyl);

3-O-(2-fluorobenzyl)-1,2-O-cyclohexylidene-5-deoxy-5-C-vinyl-alpha-D-xylofuranose (i.e., R=allyl);

3-O-(2-chlorobenzyl)-1,2-O-(2-fluoroethylidene)-5-deoxy-5-C-methyl-alpha-D-xylofuranose;

3-O-(2-chlorobenzyl)-1,2-O-{[1-(2-bromoethyl)-4-bromo]butylidene}-5-deoxy-alpha-D-xylofuranose;

3-O-(2-chlorobenzyl)-1,2-O-[1-(2-chlorobenzyl)ethylidene]-5-deoxy-5-C-ethyl-alpha-D-xylofuranose;

3-O-(2-chlorobenzyl)-1,2-O-benzylidene-5-deoxy-5,5-C-dimethyl-alpha-D-xylofuranose;

3-O-(2-chlorobenzyl)-1,2-O-{[3-phenyl-1-(2-phenethyl)]propylidene}-5-deoxy-5-C-propyl-alpha-D-xylofuranose;

3-O-(2-chlorobenzyl)-1,2-O-cyclopentylidene-5-deoxy-5-C-methylene-alpha-D-xylofuranose (i.e., R=vinyl);

3-O-(2-chlorobenzyl)-1,2-O-cyclohexylidene-5-deoxy-5-C-vinyl-alpha-D-xylofuranose (i.e., R=allyl);

3-O-(3-methoxybenzyl)-1,2-O-(2-fluoroethylidene)-5-deoxy-5-C-methyl-alpha-D-xylofuranose;

3-O-(3-methoxybenzyl)-1,2-O-cyclohexylidene-5-deoxyalpha-D-xylofuranose;

3-O-(3-methoxybenzyl)-1,2-O-cyclopentylidene-5-deoxy-5-C-ethyl-alpha-D-xylofuranose;

3-O-(3-methoxybenzyl)-1,2-O-{[3-phenyl-1-(2-phenethyl)]propylidene}-5-deoxy-5,5-C-dimethyl-alpha-D-xylofuranose;

3-O-(3-methoxybenzyl)-1,2-O-benzylidene-5-deoxy-5-C-propyl-alpha-D-xylofuranose;

3-O-(3-methoxybenzyl)-1,2-O-[1-(2-chlorobenzyl)ethylidene]-5-deoxy-5-C-methylene-alpha-D-xylofuranose (i.e., R=vinyl);

3-O-(3-methoxybenzyl)-1,2-OO{[1-(2-bromoethyl)-4-bromo)butylidene}-5-deoxy-5-C-vinyl-alpha-D-xylofuranose (i.e., R=allyl);

3-O-(2,6-dimethylbenzyl)-1,2-O-(2-fluoroethylidene)-5-deoxy-5-C-methyl-alpha-D-xylofuranose;

3-O-(2,6-dimethylbenzyl)-1,2-O-cyclopentylidene-5-deoxy-alpha-D-xylofuranose;

3-O-(2,6-dimethylbenzyl)-1,2-O-cyclohexylidene-5-deoxy-5-C-ethyl-alpha-D-xylofuranose;

3-O-(2,6-dimethylbenzyl)-1,2-O-{[3-phenyl-1-(2-phenethyl)propylidene}-5-deoxy-5,5-C-dimethyl-alpha-D-xylofuranose;

3-O-(2,6-dimethylbenzyl)-1,2-O-benzylidene-5-deoxy-5-C-propyl-alpha-D-xylofuranose;

3-O-(2,6-dimethylbenzyl)-1,2-O-[1-(2-chlorobenzyl)ethylidene]-5-deoxy-5-C-methylene-alpha-D-xylofuranose (i.e., R=vinyl);

3-O-(2,6-dimethylbenzyl)-1,2-O-{[1-(2-bromoethyl)-4-bromo]butylidene}-5-deoxy-5-C-vinyl-alpha-D-xylofuranose (i.e., R=allyl);

3-O-(2-naphthamethyl)-1,2-O-(2-fluoroethylidene)-5-deoxy-5-C-methyl-alpha-D-xylofuranose;

3-O-(2-naphthamethyl)-1,2-O-{[3-phenyl-1-(2-phenethyl)]propylidene}-5-deoxy-alpha-D-xylofuranose;

3-O-(2-naphthamethyl)-1,2-O-cyclohexylidene-5-deoxy-5-C-ethyl-alpha-D-xylofuranose;

3-O-(2-naphthamethyl)-1,2-O-cyclopentylidene-5-deoxy-5,5-C-dimethyl-alpha-D-xylofuranose;

3-O-(2-naphthamethyl)-1,2-O-{[1-(2-bromoethyl)-4-bromo]butylidene}-5-deoxy-5-C-propyl-alpha-D-xylofuranose;

3-O-(2-naphthamethyl)-1,2-O-benzylidene-5-deoxy-5-C-methylene-alpha-D-xylofuranose (i.e., R=vinyl); and 3-O-(2-naphthamethyl)-1,2-O-[1-(2-chlorobenzyl)ethylidene]-5-deoxy-5-C-vinyl-alpha-D-xylofuranose (i.e., R=allyl).

Similarly, by respectively using naphth-2-ylacetone and naphth-2-ylacetaldehyde, the corresponding 1,2-O-{1-[(naphth-2-yl)methyl]idene} and 1,2-O-[2-(naphth-2-yl)ethylidene] analogs of the above compounds can also be prepared.

EXAMPLE 2

By applying the procedures described in the above Example 1 and the appropriate starting materials, the compounds listed in Table A hereinbelow were prepared.

TABLE A

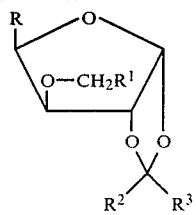

| | | | | | ELEMENTAL ANALYSIS | | | |
|---|---|---|---|---|---|---|---|---|
| | | | | | Carbon | | Hydrogen | |
| No. | R | $R^1$ | $R^2$ | $R^3$ | Calc. | Found | Calc. | Found |
| 1 | —CH₂H₃ | φ* | —CH₂F | —CH₃ | 64.85 | 63.83 | 7.14 | 7.09 |
| 2 | —CH₂CH₃ | φ | —CH₂Cl | —CH₃ | 61.44 | 61.11 | 6.77 | 6.61 |
| 3 | —CH₂CH₃ | φ | —CH₂Cl | —CH₂Cl | 55.34 | 55.81 | 5.81 | 5.74 |
| 4 | —CH₂CH₃ | φ | —CCl₃ | —H | 49.00 | 50.10 | 4.66 | 5.02 |
| 5 | —CH₂CH₃ | φ | —φ | —H | 73.60 | 73.40 | 6.79 | 7.08 |
| 6 | —CH₂CH₃ | φ | —(CH₂)₅— | | 71.67 | 72.66 | 8.23 | 8.76 |
| 7 | —CH₂CH₃ | 2-CH₃—φ | —CH₂F | —CH₃ | 65.79 | 65.38 | 7.47 | 7.69 |
| 8 | —CH₂CH₃ | 2-CH₃—φ | —(CH₂)₅— | | 72.26 | 72.83 | 8.49 | 9.12 |

*φ = phenyl

EXAMPLE 3

In this example, the compounds of Table A and the comparison compounds listed in Table B were respectively tested for pre-emergent and post-emergent activity against a variety of grasses and broad-leaf plants including one grain crop and one broad-leaf crop. The compounds tested are identified in Tables A and B hereinbelow.

PRE-EMERGENT HERBICIDE TEST

Pre-emergence herbicidal activity was determined in the following manner.

Test solutions of the respective compounds were prepared as follows:

355.5 mg of test compound was dissolved in 15 ml of acetone. 2 ml of acetone containing 110 mg of a nonionic surfactant was added to the solution. 12 ml of this stock solution was then added to 47.7 ml of water which contained the same nonionic surfactant at a concentration of 625 mg/l.

Seeds of the test vegetation were planted in a pot of soil and the test solution was sprayed uniformly onto the soil surface at a dose of either 15.6 micrograms/cm² or 27.5 micrograms/cm², as indicated in Table 1, hereinbelow. The pot was watered and placed in a greenhouse. The pot was watered intermittently and observed for seedling emergence, health of emerging seedlings, etc., for a 3-week period. At the end of this period, the herbicidal effectiveness of the compound was rated based on the physiological observations. A 0- to 100-scale was used, 0 representing no phytotoxicity, 100 representing complete kill. The results of these tests are summarized in Table 1.

POST-EMERGENT HERBICIDAL TEST the test compound was formulated in the same manner as described above for the pre-emergent test. This formulation was uniformly sprayed on 2 similar pots containing plants 2 to 3 inches tall (except wild oats, soybean and watergrass which were 3 to 4 inches tall) (approximately 15 to 25 plants per pot) either at a dose of 15.6 micrograms/cm² or 27.5 microgram/cm², as indicated in Table 1 hereinbelow. After the plants had dried, they were placed in a greenhouse and then watered intermittently at their bases as needed. The plants were observed periodically for phytotoxic effects and physiological and morphological responses to the treatment. After 3 weeks, the herbicidal effectiveness of the compound was rated based on these observations. A 0- to 100-scale was used, 0 representing no phytotoxicity, 100 representing complete kill. The results of these tests are summarized in Table 2.

TABLE 1

Pre-Emergence Herbicidal Activity
Dosage rate 15.6 micrograms/cm², unless otherwise indicated.

| | Broad-Leaf Plants % Phytotoxicity | | | | Grasses % Phytotoxicity | | | |
|---|---|---|---|---|---|---|---|---|
| Compound No. | Lambs Quarter | Mustard | Pigweed | Soybean | Crab Grass | Water Grass | Wild Oats | Rice |
| 1 | 40 | 30 | 30 | 50 | 100 | 100 | 100 | 100 |
| 2 | 30 | 20 | 30 | 0 | 100 | 100 | 60 | 40 |
| 3 | 0 | 0 | 0 | 0 | 98 | 90 | 0 | 0 |
| *4ᵃ | 45 | 0 | 45 | 0 | 98 | 100 | 45 | 0 |
| 5 | 0 | 0 | 0 | 0 | 100 | 100 | 20 | 0 |
| *6ᵃ | 60 | 0 | 50 | 0 | 100 | 100 | 88 | 25 |
| *7ᵃ | 75 | 63 | 75 | 55 | 100 | 100 | 83 | 100 |
| *8ᵃ | 65 | 0 | 65 | 0 | 100 | 100 | 65 | 50 |

*ᵃTested at 27 micrograms/cm²

TABLE 2

Post-Emergence Herbicidal Activity
Dosage rate: 15.6 micrograms/cm², unless otherwise indicated

| | Broad-Leaf Plants % Phytotoxicity | | | | Grasses % Phytotoxicity | | | |
|---|---|---|---|---|---|---|---|---|
| Compound No. | Lambs Quarter | Mustard | Pigweed | Soybean | Crab Grass | Water Grass | Wild Oats | Rice |
| 1 | 0 | 0 | 0 | 0 | 0 | 0 | 0 | 0 |
| 2 | 30 | 40 | 35 | 40 | 0 | 0 | 0 | 40 |
| 3 | 0 | 0 | 0 | 0 | 0 | 0 | 0 | 0 |
| *4ᵃ | 60 | 0 | 60 | 45 | 0 | 0 | 0 | 0 |
| 5 | 0 | 0 | 0 | 0 | 0 | 0 | 0 | 0 |
| *6ᵃ | 50 | 0 | 0 | 35 | 0 | 45 | 0 | 0 |
| *7ᵃ | 35 | 23 | 0 | 60 | 55 | 65 | 0 | 15 |
| *8ᵃ | 0 | 0 | 0 | 0 | 10 | 65 | 0 | 0 |

*ᵃTested at 27.5 micrograms/cm²

As can be seen from Tables 1 and 2, at the dosage tested the compositions of the present invention exhibited very good pre-emergence herbicide activity against grasses and in some instances also exhibited preemergence herbicide activity against broad-leaf plants and some post emergence activity.

Obviously, many modifications and variations of the invention described hereinabove and below in the claims can be made without departing from the essence and scope thereof.

What is claimed is:

1. A compound having the formula:

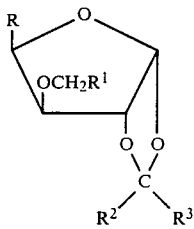

(I)

wherein R is lower alkyl having 1 through 4 carbon atoms or alkenyl having 2 through 4 carbon atoms;

$R^1$ is 2-trifluoromethylphenyl, aryl having 6 through 10 carbon atoms or substituted aryl having 1 through 4 substituents independently selected from the group of lower alkyl having 1 through 4 carbon atoms, lower alkoxy having 1 through 4 carbon atoms, cyano and halo;

one of $R^2$ or $R^3$ is lower haloalkyl having 1 through 3 halo atoms; aryl having 6 through 10 carbon atoms; substituted aryl having 1 or 2 substituents independently selected from the group of lower alkyl, lower alkoxy, halo and trifluoromethyl; arylalkyl wherein the alkyl moiety has 1 or 2 carbon atoms and the aryl moiety has 6 through 10 carbon atoms or ring substituted arylalkyl wherein the alkyl moiety has 1 or 2 carbon atoms and the aryl moiety is as defined hereinabove for substituted aryl and the other of $R^2$ or $R^3$ is hydrogen, lower alkyl, lower halo alkyl having 1 through 3 halo atoms; aryl; substituted aryl; arylalkyl; or ring substituted aryl wherein said aryl, substituted aryl, arylalkyl and substituted arylalkyl are as defined hereinabove, or $R^2$ and $R^3$ together with the carbon atom to which they are joined form a cyclopentyl or cyclohexyl group.

2. The compound of claim 1 wherein $R^1$ is aryl or monosubstituted aryl having a sole substituent selected from the group of lower alkyl, lower alkoxy, and halo.

3. The compound of claim 2 wherein $R^1$ is phenyl or monosubstituted phenyl having its sole substitutent at the 2 position.

4. The compound of claim 3 wherein R is lower alkyl.

5. The compound of claim 4 wherein R is ethyl or propyl and $R^1$ is phenyl, 2-chlorophenyl, or 2-fluorophenyl or 2-methylphenyl.

6. The compound of claim 5 wherein one of $R^2$ or $R^3$ is lower haloalkyl and the other is hydrogen lower alkyl, or lower haloalkyl.

7. The compound of claim 6 wherein one of $R^2$ or $R^3$ is hydrogen.

8. The compound of claim 7 wherein the other of $R^2$ or $R^3$ is fluoromethyl.

9. The compound of claim 1 wherein R is lower alkyl.

10. The compound of claim 9 wherein R is ethyl or propyl.

11. The compound of claim 1 wherein R is alkenyl having 2 through 4 carbon atoms.

12. The compound of claim 1 wherein one of $R^2$ or $R^3$ is lower haloalkyl and the other is hydrogen, lower alkyl or haloalkyl.

13. The compound of claim 12 wherein the total number of halogen atoms in $R^2$ plus $R^3$ is 1 or 2.

14. The compound of claim 1 wherein one of $R^2$ or $R^3$ is fluoromethyl or chloromethyl and the other hydrogen or methyl.

15. The compound of claim 14 wherein R is ethyl and $R^1$ is 2-chlorophenyl.

16. The compound of claim 14 wherein R is ethyl and $R^1$ is 2-fluorophenyl.

17. The compound of claim 14 wherein R is ethyl and $R^1$ is phenyl.

18. The compound of claim 14 wherein R is ethyl and $R^1$ is 2-methylphenyl.

19. The compound of claim 17 wherein one of $R^2$ or $R^3$ is hydrogen and the other is fluoromethyl.

20. The compound of claim 1 wherein $R^2$ and $R^3$ together with the carbon atom to which they are joined form a cyclopentyl or cyclohexyl group.

21. The compound of claim 1 wherein one of $R^2$ or $R^3$ is aryl, substituted aryl, arylalkyl, ring substituted arylalkyl and the other is hydrogen, lower alkyl, aryl, substituted aryl, arylalkyl, or ring substituted arylalkyl.

22. A herbicidal composition comprising a herbicidally effective amount of the compound of claim 1, or mixtures thereof, and a compatible carrier.

23. A method for treating undesired vegetation which comprises supplying a herbicidally effective amount of the compound of claim 1 or mixtures thereof, to the foliage and/or growth medium of said vegetation.

24. The method of claim 23, wherein said vegetation is grass.

25. A plant growth regulating composition comprising a compatible carrier and a plant growth regulating effective amount of the compound of claim 1 or mixtures thereof.

26. A method for advantageously altering the growth pattern of plants which comprises contacting the seeds or foliage of such plants with a plant growth regulating effective amount of a compound according to claim 1 or mixtures thereof.

27. A herbicidal composition comprising a preemergence herbicidal effective amount of a compound according to claim 1, or mixture thereof, and a compatible carrier.

28. A method for treating grasses which comprises applying a pre-emergence herbicidally effective amount of a compound according to claim 1 or mixtures thereof to the growth medium or potential growth medium of said grasses.

* * * * *